United States Patent [19]
Subramaniam et al.

[11] Patent Number: 5,981,217
[45] Date of Patent: *Nov. 9, 1999

[54] DNA ENCODING TGF-β INDUCIBLE EARLY FACTOR-1 (TIEF-1), A GENE EXPRESSED BY OSTEOBLASTS

[75] Inventors: Malayannan Subramaniam, Zumbrota; Thomas C. Spelsberg, Rochester, both of Minn.

[73] Assignee: Mayo Foundation for Medical Education and Research, Rochester, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/570,227

[22] Filed: Dec. 11, 1995

[51] Int. Cl.$^6$ .............................. C12P 21/06; C12N 1/20; C12N 15/00; C07H 21/04
[52] U.S. Cl. .................. 435/69.1; 435/252.3; 435/320.1; 435/325; 536/23.5; 536/24.31
[58] Field of Search .............................. 435/6, 69.1, 91.2, 435/172.3, 240.1, 320.1, 325; 536/22.1, 23.1, 24.3, 24.31, 24.33, 23.5; 935/6, 8, 23, 55, 77, 78

[56] References Cited

U.S. PATENT DOCUMENTS 5,444,164  8/1995  Porchio et al. .................. 536/23.5

FOREIGN PATENT DOCUMENTS

| 0495674 | 7/1992 | European Pat. Off. | C12N 12/12 |
| 0555989 | 8/1993 | European Pat. Off. | C12N 15/12 |
| 90/02203 | 3/1990 | WIPO | C12Q 1/68 |

OTHER PUBLICATIONS

Stratagene Catalog, pp. 146–161, 1993.
Koskinen et. al. Growth Factors 5:283–293, 1991.
DuBois et al. Cell Growth and Differentiation 6: 52–529, May 1995.
Ohba et al. The Journal of Cell Biology 126:1079–1088, Aug. 1994.
Liu et al. Crit. Rev. Oncog. 7:101–125, 1996.
Arnoletti, J.P., et al., "Thrombospondin and Transforming Growth Factor–Beta 1 Increase Expression of Urokinase–type Plasminogen Activator and Plasminogen Activator Inhibitor–1 in Human MDA–MB 231 Breast Cancer Cells", *Cancer*, 76, 998–1005, (Sep. 15, 1995).
Hagen, G., et al., "Cloning by Recognition Site Screening of Two Novel GT Box Binding Proteins: A Family of Sp1 Related Genes", *Nucleic Acids Research*, 20, 5519–5525, (Oct. 15, 1992).
Kadonaga, J.T., et al., "Isolation of cDNA Encoding Transcription Factor Sp1 and Functional Analysis of the DNA Binding Domain", *Cell*, 51, 1079–1090, (Dec. 24, 1987).
Lafon, C., et al., "Early gene responses associated with transforming growth factor–B1 growth inhibition and auto-induction in MCF–7 breast adenocarcinoma cells", *Biochimica et Biophysica Acta*, 1266, 288–295, (1995).

Snyder, R., et al., "Cellular and molecular correlates in human breast tumor progression", *Proceedings of the American Association for Cancer Research*, vol. 36, p. 8, (Mar. 1995).
Subramaniam, M., et al., "Identification of a novel TGF–B regulated gene encoding a putatitve zinc finger protein in human osteoblasts", *Nucleic Acids Research*, 23, 4907–4912, (Nov. 2, 1995).
Takenaka, I.M., et al., "Transforming growth factor–B1 rapidly induces Hsp70 and Hsp90 Molecular Chaperones in Cultured Chicken Embryo Cells", *Journal of Cellular Physiology*, 152, 568–577, (1992).
G. R. Mundy, "Factors Regulating Bone Resorbing and Bone Forming Cells", In: *Bone Remodeling and Its Disorders*, Martin Dunitz, Ltd, London, pp. 56–57, (1995).
M. Noda, et al., "Transcriptional Regulation of Osteopontin Production in Rat Osteosarcoma cells by Type β transforming Growth Factor", *J. Biol. Chem.*, 263, 13916–13921, (Sep., 1988).
M. Noda, et al., "Type β Transforming Growth Factor (TGFβ) Regulation of Alkaline Phosphatase Expression and Other Phenotype–Related mRNAs in Osteoblast Rat Osteosarcoma Cells", *J. Cell. Physiol.*, 133, 426–437, (1987).
M. J. Oursler, et al., "Glucocorticoid–Induced Activation of Latent Transforming Growth Factor–β by Normal Human Osteoblast–Like Cells", *Endocrinology*, 133, 2187–2196, (1993).
M. J. Oursler, et al, "Modulation of Transforming Growth Factor–β Production in Normal Human Osteoblast–Like Cells by 17β–Estradiol and Parathyroid Hormone", *Endocrinology*, 129, 3313–3320, (1991).
J. Pfeilschifter, et al., "Modulation of Type β Transforming Grwoth Factor Activity in Bone Cultures by Osteotropic Hormones", *Proc. Natl. Acad. Sci. USA*, 84, 2024–2028, (Apr., 1987).
A. B. Roberts, et al., "Physiological Actions and Clinical Applications of Transforming Growth Factor–β (TGF–β)", *Growth Factors*, 8, 1–9, (1993).
P. G. Robley, et al., "Osteoblasts Synthesize and Respond to Transforming Growth Factor–Type β (TGF–β) In Vitro", *J. Cell Biology*, 105, 457–463, (Jul., 1987).
M. Sabramaniam, et al., "Characterization of a TGF–β Regulated Gene Encoding a Putative Zinc Finger Protein and SRC Substrate in Human Osteoblasts", *J. Bone Mineral Res.*, 10(S1), Abstract 21, p. S144, (Sep., 1995).

(List continued on next page.)

*Primary Examiner*—Bradley L. Sisson
*Attorney, Agent, or Firm*—Schwegan, Lundberg, Woessner & Kluth, P.A.

[57] ABSTRACT

An isolated and purified DNA molecule encoding TGF-β inducible early factor-1 (TIEF-1) is provided. A method of isolating a growth factor- or differentiation factor-inducible gene is also provided.

19 Claims, 11 Drawing Sheets

OTHER PUBLICATIONS

M. Subramaniam, et al., "Identification of a Novel TGF-β Inducible Early Gene in Human Osteoblasts", *J .Bone Mineral Res.*, 9(S1), Abstract No. 81, p. S141, (Sep., 1994).

M. Subramaniam, et al., "TGF-β Regulation of Nuclear Proto–Oncogenes and TGF-β Gene Expression in Normal Human Osteoblast–Like Cells", *J. Cell. Biochem.*, 57, 52–61, (1995).

K. R. Tau, et al., "Estrogen Upregulation of a Novel Transforming Growth Factor-β Inducible Gene in a Human Osteoblastic Cell Line", *J. Bone Mineral Res.*, 10(S1), Abstract No. T547, p. S491, (Sep., 1995).

J. L. Wrana, et al., "Differential Effects of Transforming Grwoth Factor-β on the Synthesis of Extracellular Matrix Proteins by Normal Fetal Rat Calvarial Bone Cell Populations", *J. Cell Biol.*,106, 915–924, (Mar., 1988).

Shibanuma et. al. J.Biol.Chem. 267(15):10219–10224 (May 25, 1992).

Shibanuma et al. J.Biol.Chem. 269(43):26767–26774 (Oct. 28, 1994).

Blok et al. Mol. Endocrin. 9(11):1610–1620 (Nov. 1995).

New England BioLabs Catalog 1993/1994 pp. 97 and 112.

Sambrook et. al., Editors of Molecular Cloning: A Laboratory Manual. (1989) pp. 16.3–16.31, 16.56–16.58, 17.2–17.25, 17.36–17.37 ATCC Catalog, 1991 pp. 13–15.

```
   1 GAATTCGGCACGAGCGCCCGTCTGTGGCCAAGCAGCCAGCAGCCTAGCAGCCAGTCAGCT
  61 TGCCGCCGGCGGCCAAGCAGCCAACCATGCTCAACTTCGGTGCCTCTCTCCAGCAGACTG
                                  M  L  N  F  G  A  S  L  Q  Q  T  A     12
 121 CGGAGGAAAGAATGGAAATGATTTCTGAAAGGCCAAAAGAGAGTATGTATTCCTGGAACA
      E  E  R  M  E  M  I  S  E  R  P  K  E  S  M  Y  S  W  N  K     32
 181 AAACTGCAGAGAAAAGTGATTTTGAAGCTGTAGAAGCACTTATGTCAATGAGCTGCAGTT
      T  A  E  K  S  D  F  E  A  V  E  A  L  M  S  M  S  C  S  W     52
 241 GGAAGTCTGATTTTAAGAAATACGTTGAAAACAGACCTGTTACACCAGTATCTGATTTGT
      K  S  D  F  K  K  Y  V  E  N  R  P  V  T  P  V  S  D  L  S     72
 301 CAGAGGAAGAGAATCTGCTTCCGGGAACACCTGATTTTCATACAATCCCAGCATTTTGTT
      E  E  E  N  L  L  P  G  T  P  D  F  H  T  I  P  A  F  C  L     92
 361 TGACTCCACCTTACAGTCCTTCTGACTTTGAACCCTCTCAAGTGTCAAATCTGATGGCAC
      T  P  P  Y  S  P  S  D  F  E  P  S  Q  V  S  N  L  M  A  P    112
 421 CAGCGCCATCTACTGTACACTTCAAGTCACTCTCAGATACTGCCAAACCTCACATTGCCG
      A  P  S  T  V  H  F  K  S  L  S  D  T  A  K  P  H  I  A  A    132
 481 CACCTTTCAAAGAGGAAGAAAAGAGCCCAGTATCTGCCCCCAAACTCCCCAAAGCTCAGG
      P  F  K  E  E  E  K  S  P  V  S  A  P  K  L  P  K  A  Q  A    152
 541 CAACAAGTGTGATTCGTCATACAGCTGATGCCCAGCTATGTAACCACCAGACCTGCCCAA
      T  S  V  I  R  H  T  A  D  A  Q  L  C  N  H  Q  T  C  P  M    172
 601 TGAAAGCAGCCAGCATCCTCAACTATCAGAACAATTCTTTTAGAAGAAGAACCCACCTAA
      K  A  A  S  I  L  N  Y  Q  N  N  S  F  R  R  R  T  H  L  N    192
 661 ATGTTGAGGCTGCAAGAAAGAACATACCATGTGCCGCTGTGTCACCAAACAGATCCAAAT
      V  E  A  A  R  K  N  I  P  C  A  A  V  S  P  N  R  S  K  C    212
 721 GTGAGAGAAACACAGTGGCAGATGTTGATGAGAAAGCAAGTGCTGCACTTTATGACTTTT
      E  R  N  T  V  A  D  V  D  E  K  A  S  A  A  L  Y  D  F  S    232
 781 CTGTGCCTTCCTCAGAGACGGTCATCTGCAGGTCTCAGCCAGCCCTGTGTCCCCACAAC
      V  P  S  S  E  T  V  I  C  R  S  Q  P  A  P  V  S  Q  Q      252
 841 AGAAGTCAGTGTTGGTCTCTCCACCTGCAGTATCTGCAGGGGGAGTGCCACCTATGCCGG
      K  S  V  L  V  S  P  P  A  V  S  A  G  G  V  P  P  M  P  V    272
 901 TCATCTGCCAGATGGTTCCCCTTCCTGCCAACAACCCTGTTGTGACAACAGTCGTTCCCA
      I  C  Q  M  V  P  L  P  A  N  N  P  V  V  T  T  V  V  P  S    292
 961 GCACTCCTCCCAGCCAGCCACCAGCCGTTTGCCCCCTGTTGTGTTCATGGGCACACAAG
      T  P  P  S  Q  P  P  A  V  C  P  P  V  V  F  M  G  T  Q  V    312
1021 TCCCCAAAGGCGCTGTCATGTTTGTGGTACCCCAGCCCGTTGTGCAGAGTTCAAAGCCTC
      P  K  G  A  V  M  F  V  V  P  Q  P  V  V  Q  S  S  K  P  P    332
1081 CGGTGGTGAGCCCGAATGGCACCAGACTCTCTCCCATTGCCCCTGCTCCTGGGTTTCCC
      V  V  S  P  N  G  T  R  L  S  P  I  A  P  A  P  G  F  S  P    352
1141 CTTCAGCAGCAAAAGTCACTCCTCAGATTGATTCATCAAGGATAAGGAGTCACATCTGTA
      S  A  A  K  V  T  P  Q  I  D  S  S  R  I  R  S  H  I  C  S    372
1201 GCCACCCAGGATGTGGCAAGACATACTTTAAAAGTTCCCATCTGAAGGCCCACACGAGGA
      H  P  G  C  G  K  T  Y  F  K  S  S  H  L  K  A  H  T  R  T    392
1261 CGCACACAGGAGAAAAGCCTTTCAGCTGTAGCTGGAAAGGTTGTGAAAGGAGGTTTGCCC
      H  T  G  E  K  P  F  S  C  S  W  K  G  C  E  R  R  F  A  R    412
1321 GTTCTGATGAACTGTCCAGACACAGGCGAACCCACACGGGTGAGAAGAAATTTGCGTGCC
      S  D  E  L  S  R  H  R  R  T  H  T  G  E  K  K  F  A  C  P    432
1381 CCATGTGTGACCGGCGGTTCATGAGGAGTGACCATTTGACCAAGCATGCCCGGCGCCATC
      M  C  D  R  R  F  M  R  S  D  H  L  T  K  H  A  R  R  H  L    452
1441 TATCAGCCAAGAAGCTACCAAACTGGCAGATGGAAGTGAGCAAGCTAAATGACATTGCTC
      S  A  K  K  L  P  N  W  Q  M  E  V  S  K  L  N  D  I  A  L    472
1501 TACCTCCAACCCCTGCTCCCACACAGTGACAGACCGGAAAGTGAAGAGTCAGAACTAACT
                                                                   480
      P  P  T  P  A  P  T  Q  *
1561 TTGGTCTCAGCGGGAGCCAGTGGTGATGTAAAAATGCTTCCACTGCAAGTCTGTGGCCCC
1621 ACAACGTGGGCTTAAAGCAGAAGCCCCACAGCCTGGCACGAAGGCCCCGCCTGGGTTAGG
1681 TGACTAAAAGGGCTTCGGCCACAGGCAGGTCACAGAAAGGCAGGTTTCATTTCTTATCAC
1741 ATAAGAGAGATGAGAAAGCTTTTATTCCTTTGAATATTTTTTGAAGGTTTCAGATGAGGT
1801 CAACACAGGTAGCACAGATTTTGAATCTGTGTGCATATTTGTTACTTTACTTTTGCTGTT
1861 TATACTTGAGACCAACTTTTCAATGTGATTCTTCTAAAGCACTGGTTTCAAGAATATGGA
1921 AGCTGGAAGGAAATAAACATTACGGTACAGACATGGAGATGTAAAATGAGTTTGTATTAT
1981 TACAAATATTGTCATCTTTTTCTAGAGTTATCTTCTTTATTATTCCTAGTCTTTCCAGTC
2041 AACATCGTGGATGTAGTGATTAAATATATCTAGAACATCTATCATTTTTACACTATTGTGAAT
2101 ATTTGGAATTGAACGACTGTATATTGCTAAGAGGGCCCAAAGAATTGGAATCCTCCTTAA
2161 TTTAATTGCTTTGAAGCATAGCTACAATTTGTTTTTGCATTTTTGTTTTGAAAGTTTAAC
2221 AAATGACTGTATCTAGGCATTTCATTATGCTTTGAACTTTAGTTTGCCTGCAGTTTCTTG
2281 TGTAGATTTGAAAATTGTATACCAATGTGTTTTCTGTAGACTCTAAGATACACTGCACTT
2341 TGTTTAGAAAAAAACTGAAGATGAAATATATATTGTAAAGAAGGGATATTAAGAATCTT
2401 AGATAACTTCTTGAAAAAGATGGCTTATGTCATCAGTAAAGTACCTTTATGTTATGAGGA
2461 TATAATGTGTGCTTTATTGAATTAGAAAATTAGTGACCATTATTCACAGGTGGACAAATG
2521 TTCGTCCTGTTAATTTATAGGAGTTTTTGGGGATGTGGAGGTAGTTGGGTAGAAAAATT
2581 ATTAGAACATTCACTTTTGTTAACAGTATTTCTCTTTTATTCTGTTATATAGTGGATGAT
2641 ATACACAGTGGCAAAACAAAAGTACATTGCTTAAAATATATAGTGAAAAATGTCACTATA
2701 TCTTCCCATTTAACATTGTTTTTGTATATTGGGTGTAGATTTCTGACATCAAAACTTGGA
2761 CCCTTGGAAAACAAAAGTTTTAATTAAAAAAAATCCTTGTGACTTACAATTTGCACAATA
2821 TTTCTTTTGTTGTACTTTATATCTTGTTTACAATAAAGAATTCCCTTTGGCAAAAAAAAA
2881 A
```

FIG. 4

```
371                                                                                                          447
TIEF     CSHPGCGKTYFKSSHLKAHTRTHTGEKPFSCSWKGCERRFARSDELSRHRRTHTGEKKFEACPMCDRRFMRSDHLTKH
SPR-2    CHIPGCGKVYGKTSHLRAHLRWHSGERPFVCNWMYCGKRFTRSDELQRHRRTHTGEKKFVCPECSKRFMRSDHLAKH
Sp3      CHIPGCGKVYGKTSHLRAHLRWHSGERPFVCNWMYCGKRFTRSDELQRHRRTHTGEKKFVCPECSKRFMRSDHLSKH
SPR-1    CHIEGCGKVYGKTSHLRAHLRWHTGERPFICNWMFCGKRFTRSDELQRHRRTHTGEKRFECPECSKRFMRSDHLSKH
Sp1      CHIQGCGKVYGKTSHLRAHLRWHTGERPFMCTWSYCGKRFTRSDELQRHKRTHTGEKKFACPECPKRFMRSDHLALH
BTEB     CDYPGCTKVYTKSSHLKAHLRTHTGEKPYKCTWEGCDWRFARSDELTRHYRKHTGAKPFQCGVCNRSFSRSDHLALH
MUS Krp  CGHEGCGKSYSKSSHLKAHLRTHTGEKPYACSWDGCDWRFARSDELTRHYRKHTGHRPFCCGLCPRAFSRSDHLALH
Sp2      CHIPDCGKTFRKTSLLRAHVRLHTGERPFVCNWFFCGKRFTRSDELQRHARTHTGDKRFECAQCQKRFMRSDHLTKH
WT-1     CAYPGCNKRYFKLSHLQMHSRKHTGEKPYQCDFKDCERRFSRSDQLKRHQRRHTGVKPFQCKTCQRKFSRSDHLKTH
```

FIG. 5

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 2881 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GAATTCGGCA CGAGCGCCCG TCTGTGGCCA AGCAGCCAGC AGCCTAGCAG CCAGTCAGCT     60

TGCCGCCGGC GGCCAAGCAG CCAACCATGC TCAACTTCGG TGCCTCTCTC CAGCAGACTG    120

CGGAGGAAAG AATGGAAATG ATTTCTGAAA GGCCAAAAGA GAGTATGTAT TCCTGGAACA    180

AAACTGCAGA GAAAAGTGAT TTTGAAGCTG TAGAAGCACT TATGTCAATG AGCTGCAGTT    240

GGAAGTCTGA TTTTAAGAAA TACGTTGAAA ACAGACCTGT TACACCAGTA TCTGATTTGT    300

CAGAGGAAGA GAATCTGCTT CCGGGAACAC CTGATTTTCA TACAATCCCA GCATTTTGTT    360

TGACTCCACC TTACAGTCCT TCTGACTTTG AACCCTCTCA AGTGTCAAAT CTGATGGCAC    420

CAGCGCCATC TACTGTACAC TTCAAGTCAC TCTCAGATAC TGCCAAACCT CACATTGCCG    480

CACCTTTCAA AGAGGAAGAA AAGAGCCCAG TATCTGCCCC CAAACTCCCC AAAGCTCAGG    540

CAACAAGTGT GATTCGTCAT ACAGCTGATG CCCAGCTATG TAACCACCAG ACCTGCCCAA    600

TGAAAGCAGC CAGCATCCTC AACTATCAGA ACAATTCTTT TAGAAGAAGA ACCCACCTAA    660

ATGTTGAGGC TGCAAGAAAG AACATACCAT GTGCCGCTGT GTCACCAAAC AGATCCAAAT    720

GTGAGAGAAA CACAGTGGCA GATGTTGATG AGAAAGCAAG TGCTGCACTT TATGACTTTT    780

CTGTGCCTTC CTCAGAGACG GTCATCTGCA GGTCTCAGCC AGCCCCTGTG TCCCCACAAC    840

AGAAGTCAGT GTTGGTCTCT CCACCTGCAG TATCTGCAGG GGGAGTGCCA CCTATGCCGG    900

TCATCTGCCA GATGGTTCCC CTTCCTGCCA ACAACCCTGT TGTGACAACA GTCGTTCCCA    960

GCACTCCTCC CAGCCAGCCA CCAGCCGTTT GCCCCCTGT TGTGTTCATG GGCACACAAG   1020

TCCCCAAAGG CGCTGTCATG TTTGTGGTAC CCCAGCCCGT TGTGCAGAGT TCAAAGCCTC   1080

CGGTGGTGAG CCCGAATGGC ACCAGACTCT CTCCCATTGC CCCTGCTCCT GGGTTTTCCC   1140

CTTCAGCAGC AAAAGTCACT CCTCAGATTG ATTCATCAAG GATAAGGAGT CACATCTGTA   1200

GCCACCCAGG ATGTGGCAAG ACATACTTTA AAAGTTCCCA TCTGAAGGCC CACACGAGGA   1260

CGCACACAGG AGAAAAGCCT TTCAGCTGTA GCTGGAAAGG TTGTGAAAGG AGGTTTGCCC   1320

GTTCTGATGA ACTGTCCAGA CACAGGCGAA CCCACACGGG TGAGAAGAAA TTTGCGTGCC   1380

CCATGTGTGA CCGGCGGTTC ATGAGGAGTG ACCATTTGAC CAAGCATGCC CGGCGCCATC   1440

TATCAGCCAA GAAGCTACCA AACTGGCAGA TGGAAGTGAG CAAGCTAAAT GACATTGCTC   1500

TACCTCCAAC CCCTGCTCCC ACACAGTGAC AGACCGGAAA GTGAAGAGTC AGAACTAACT   1560

TTGGTCTCAG CGGGAGCCAG TGGTGATGTA AAAATGCTTC CACTGCAAGT CTGTGGCCCC   1620

ACAACGTGGG CTTAAAGCAG AAGCCCCACA GCCTGGCACG AAGGCCCCGC CTGGGTTAGG   1680

TGACTAAAAG GGCTTCGGCC ACAGGCAGGT CACAGAAAGG CAGGTTTCAT TTCTTATCAC   1740

ATAAGAGAGA TGAGAAAGCT TTTATTCCTT TGAATATTTT TTGAAGGTTT CAGATGAGGT   1800

CAACACAGGT AGCACAGATT TGAATCTGT GTGCATATTT GTTACTTTAC TTTTGCTGTT   1860

TATACTTGAG ACCAACTTTT CAATGTGATT CTTCTAAAGC ACTGGTTTCA AGAATATGGA   1920

AGCTGGAAGG AAATAAACAT TACGGTACAG ACATGGAGAT GTAAAATGAG TTTGTATTAT   1980

TACAAATATT GTCATCTTTT TCTAGAGTTA TCTTCTTTAT TATTCCTAGT CTTTCCAGTC   2040

AACATCGTGG ATGTAGTGAT TAAATATATC TAGAACTATC ATTTTTACAC TATTGTGAAT   2100

ATTTGGAATT GAACGACTGT ATATTGCTAA GAGGGCCCAA AGAATTGGAA TCCTCCTTAA   2160

TTTAATTGCT TTGAAGCATA GCTACAATTT GTTTTTGCAT TTTTGTTTTG AAAGTTTAAC   2220

AAATGACTGT ATCTAGGCAT TTCATTATGC TTTGAACTTT AGTTTGCCTG CAGTTTCTTG   2280

TGTAGATTTG AAAATTGTAT ACCAATGTGT TTTCTGTAGA CTCTAAGATA CACTGCACTT   2340

TGTTTAGAAA AAAAACTGAA GATGAAAATAT ATATTGTAAA GAAGGGATAT TAAGAATCTT   2400
```

```
AGATAACTTC TTGAAAAAGA TGGCTTATGT CATCAGTAAA GTACCTTTAT GTTATGAGGA  2460

TATAATGTGT GCTTTATTGA ATTAGAAAAT TAGTGACCAT TATTCACAGG TGGACAAATG  2520

TTCGTCCTGT TAATTTATAG GAGTTTTTTG GGGATGTGGA GGTAGTTGGG TAGAAAAATT  2580

ATTAGAACAT TCACTTTTGT TAACAGTATT TCTCTTTTAT TCTGTTATAT AGTGGATGAT  2640

ATACACAGTG GCAAAACAAA AGTACATTGC TTAAAATATA TAGTGAAAAA TGTCACTATA  2700

TCTTCCCATT TAACATTGTT TTTGTATATT GGGTGTAGAT TTCTGACATC AAAACTTGGA  2760

CCCTTGGAAA ACAAAAGTTT TAATTAAAAA AAATCCTTGT GACTTACAAT TTGCACAATA  2820

TTTCTTTTGT TGTACTTTAT ATCTTGTTTA CAATAAAGAA TTCCCTTTGG CAAAAAAAAA  2880

A                                                                  2881
```

(2) INFORMATION FOR SEQ ID NO:2:

(i) SEQUENCE CHARACTERISTICS:
        (A) LENGTH: 480 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Leu Asn Phe Gly Ala Ser Leu Gln Gln Thr Ala Glu Glu Arg Met
 1               5                  10                  15

Glu Met Ile Ser Glu Arg Pro Lys Glu Ser Met Tyr Ser Trp Asn Lys
            20                  25                  30

Thr Ala Glu Lys Ser Asp Phe Glu Ala Val Glu Ala Leu Met Ser Met
        35                  40                  45

Ser Cys Ser Trp Lys Ser Asp Phe Lys Lys Tyr Val Glu Asn Arg Pro
    50                  55                  60

Val Thr Pro Val Ser Asp Leu Ser Glu Glu Asn Leu Leu Pro Gly
 65                  70                  75                  80

Thr Pro Asp Phe His Thr Ile Pro Ala Phe Cys Leu Thr Pro Pro Tyr
                85                  90                  95

Ser Pro Ser Asp Phe Glu Pro Ser Gln Val Ser Asn Leu Met Ala Pro
            100                 105                 110

Ala Pro Ser Thr Val His Phe Lys Ser Leu Ser Asp Thr Ala Lys Pro
        115                 120                 125

His Ile Ala Ala Pro Phe Lys Glu Glu Glu Lys Ser Pro Val Ser Ala
    130                 135                 140

Pro Lys Leu Pro Lys Ala Gln Ala Thr Ser Val Ile Arg His Thr Ala
145                 150                 155                 160

Asp Ala Gln Leu Cys Asn His Gln Thr Cys Pro Met Lys Ala Ala Ser
                165                 170                 175

Ile Leu Asn Tyr Gln Asn Asn Ser Phe Arg Arg Arg Thr His Leu Asn
            180                 185                 190

Val Glu Ala Ala Arg Lys Asn Ile Pro Cys Ala Ala Val Ser Pro Asn
        195                 200                 205

Arg Ser Lys Cys Glu Arg Asn Thr Val Ala Asp Val Asp Glu Lys Ala
    210                 215                 220

Ser Ala Ala Leu Tyr Asp Phe Ser Val Pro Ser Ser Glu Thr Val Ile
225                 230                 235                 240

Cys Arg Ser Gln Pro Ala Pro Val Ser Pro Gln Gln Lys Ser Val Leu
                245                 250                 255
```

```
Val Ser Pro Pro Ala Val Ser Ala Gly Gly Val Pro Pro Met Pro Val
            260                 265                 270

Ile Cys Gln Met Val Pro Leu Pro Ala Asn Asn Pro Val Val Thr Thr
        275                 280                 285

Val Val Pro Ser Thr Pro Pro Ser Gln Pro Pro Ala Val Cys Pro Pro
    290                 295                 300

Val Val Phe Met Gly Thr Gln Val Pro Lys Gly Ala Val Met Phe Val
305                 310                 315                 320

Val Pro Gln Pro Val Val Gln Ser Ser Lys Pro Pro Val Val Ser Pro
                325                 330                 335

Asn Gly Thr Arg Leu Ser Pro Ile Ala Pro Ala Pro Gly Phe Ser Pro
            340                 345                 350

Ser Ala Ala Lys Val Thr Pro Gln Ile Asp Ser Ser Arg Ile Arg Ser
        355                 360                 365

His Ile Cys Ser His Pro Gly Cys Gly Lys Thr Tyr Phe Lys Ser Ser
    370                 375                 380

His Leu Lys Ala His Thr Arg Thr His Thr Gly Glu Lys Pro Phe Ser
385                 390                 395                 400

Cys Ser Trp Lys Gly Cys Glu Arg Arg Phe Ala Arg Ser Asp Glu Leu
                405                 410                 415

Ser Arg His Arg Arg Thr His Thr Gly Glu Lys Lys Phe Ala Cys Pro
            420                 425                 430

Met Cys Asp Arg Arg Phe Met Arg Ser Asp His Leu Thr Lys His Ala
        435                 440                 445

Arg Arg His Leu Ser Ala Lys Lys Leu Pro Asn Trp Gln Met Glu Val
    450                 455                 460

Ser Lys Leu Asn Asp Ile Ala Leu Pro Pro Thr Pro Ala Pro Thr Gln
465                 470                 475                 480

(2) INFORMATION FOR SEQ ID NO:3:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

CCTGTAATCC                                                      10

(2) INFORMATION FOR SEQ ID NO:4:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Cys His Ile Pro Gly Cys Gly Lys Val Tyr Gly Lys Thr Ser His Leu
1               5                   10                  15

Arg Ala His Leu Arg Trp His Ser Gly Glu Arg Pro Phe Val Cys Asn
            20                  25                  30

Trp Met Tyr Cys Gly Lys Arg Phe Thr Arg Ser Asp Glu Leu Gln Arg
        35                  40                  45
```

```
His Arg Arg Thr His Thr Gly Glu Lys Lys Phe Val Cys Pro Glu Cys
     50                  55                  60

Ser Lys Arg Phe Met Arg Ser Asp His Leu Ala Lys His
 65                  70                  75
```

(2) INFORMATION FOR SEQ ID NO:5:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Cys His Ile Gln Gly Cys Gly Lys Val Tyr Gly Lys Thr Ser His Leu
 1                   5                  10                  15

Arg Ala His Leu Arg Trp His Thr Gly Glu Arg Pro Phe Met Cys Thr
                 20                  25                  30

Trp Ser Tyr Cys Gly Lys Arg Phe Thr Arg Ser Asp Glu Leu Gln Arg
             35                  40                  45

His Lys Arg Thr His Thr Gly Glu Lys Lys Phe Ala Cys Pro Glu Cys
     50                  55                  60

Pro Lys Arg Phe Met Arg Ser Asp His Leu Ser Lys His
 65                  70                  75
```

(2) INFORMATION FOR SEQ ID NO:6:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Cys His Ile Glu Gly Cys Gly Lys Val Tyr Gly Lys Thr Ser His Leu
 1                   5                  10                  15

Arg Ala His Leu Arg Trp His Thr Gly Glu Arg Pro Phe Thr Cys Asn
                 20                  25                  30

Trp Met Phe Cys Glu Lys Arg Phe Thr Arg Ser Asp Glu Leu Gln Arg
             35                  40                  45

His Arg Arg Thr His Thr Gly Glu Lys Arg Phe Glu Cys Pro Glu Cys
     50                  55                  60

Ser Lys Arg Phe Met Arg Ser Asp His Leu Ser Lys His
 65                  70                  75
```

(2) INFORMATION FOR SEQ ID NO:7:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Cys His Ile Gln Gly Cys Gly Lys Val Tyr Gly Lys Thr Ser His Leu
 1                   5                  10                  15

Arg Ala His Leu Arg Trp His Thr Gly Glu Arg Pro Phe Met Cys Thr
                 20                  25                  30
```

Trp Ser Tyr Cys Gly Lys Arg Phe Thr Arg Ser Asp Glu Leu Gln Arg
            35                  40                  45

His Lys Arg Thr His Thr Gly Glu Lys Lys Phe Ala Cys Pro Glu Cys
        50                  55                  60

Pro Lys Arg Phe Met Arg Ser Asp His Leu Ser Lys His
65                  70                  75

(2) INFORMATION FOR SEQ ID NO:8:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Cys Asp Tyr Pro Gly Cys Thr Lys Val Tyr Thr Lys Ser Ser His Leu
1               5                   10                  15

Lys Ala His Lys Arg Thr His Thr Gly Glu Lys Pro Trp Lys Cys Thr
            20                  25                  30

Trp Glu Gly Cys Asp Trp Arg Phe Ala Arg Ser Asp Glu Leu Thr Arg
            35                  40                  45

His Tyr Arg Lys His Thr Gly Ala Lys Pro Phe Gln Cys Gly Val Cys
        50                  55                  60

Asn Arg Ser Phe Ser Arg Ser Asp His Leu Ala Leu His
65                  70                  75

(2) INFORMATION FOR SEQ ID NO:9:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Cys Gly His Glu Gly Cys Gly Lys Ser Tyr Ser Lys Ser Ser His Leu
1               5                   10                  15

Lys Ala His Leu Arg Thr His Thr Gly Glu Lys Pro Tyr Ala Cys Ser
            20                  25                  30

Trp Asp Gly Cys Asp Trp Arg Phe Ala Arg Ser Asp Glu Leu Thr Arg
            35                  40                  45

His Tyr Arg Lys His Thr Gly His Arg Pro Phe Cys Cys Gly Leu Cys
        50                  55                  60

Pro Arg Ala Phe Ser Arg Ser Asp His Leu Ala Leu His
65                  70                  75

(2) INFORMATION FOR SEQ ID NO:10:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Cys His Ile Pro Asp Cys Gly Lys Thr Phe Arg Lys Thr Ser Leu Leu
1               5                   10                  15

Arg Ala His Val Arg Leu His Thr Gly Glu Arg Pro Phe Val Cys Asn
                20                  25                  30

Trp Phe Phe Cys Gly Lys Arg Phe Thr Arg Ser Asp Glu Leu Gln Arg
            35                  40                  45

His Ala Arg Thr His Thr Gly Asp Lys Arg Phe Glu Cys Ala Gln Cys
        50                  55                  60

Gln Lys Arg Phe Met Arg Ser Asp His Leu Thr Lys His
65                  70                  75

(2) INFORMATION FOR SEQ ID NO:11:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Cys Ala Tyr Pro Gly Cys Asn Lys Arg Tyr Phe Lys Leu Ser His Leu
1               5                   10                  15

Gln Met His Ser Arg Lys His Thr Gly Glu Lys Pro Tyr Gln Cys Asp
                20                  25                  30

Phe Lys Asp Cys Glu Arg Arg Phe Ser Arg Ser Asp Gln Leu Lys Arg
            35                  40                  45

His Gln Arg Arg His Thr Gly Val Lys Pro Phe Gln Cys Lys Thr Cys
        50                  55                  60

Gln Arg Lys Phe Ser Arg Ser Asp His Leu Lys Thr His
65                  70                  75
```

DNA ENCODING TGF-β INDUCIBLE EARLY FACTOR-1 (TIEF-1), A GENE EXPRESSED BY OSTEOBLASTS

STATEMENT OF GOVERNMENT RIGHTS

The present invention was made with the support of the United States Government via grants from the National Institutes of Health (AG04875 and AR41652). The Government has certain rights in the invention.

BACKGROUND OF THE INVENTION

The most abundant source of transforming growth factorβ (TGF-β) in the body is bone. The process of new bone formation in young adults, which involves the removal of bone by osteoclasts (OC) and replacement of that bone by osteoblasts (OB), appears to be tightly regulated by locally produced factors. TGF-β is a prime candidate for one of these factors as both OB and OC are known to produce TGF-β.

The production and activation of TGF-β is regulated by estrogen, parathyroid hormone, glucocorticoids, and other bone regulatory agents including TGF-β itself (Oursler et al, *Endocrinology*, 129, 3313 (1991); Oursler et al., *Endocrinology*, 133, 2187 (1993); Subramaniam et al., *J. Cell. Biochem.*, 51, 52 (1995)). Disregulation of TGF-β production and/or activation may be involved in bone diseases (Mundy, In: *Bone Remodeling and its Disorders*, Dunitz (ed.), U.K., pp. 56–65 (1995); Roberts et al., *Growth Factors*, 8, 1 (1993)). Thus, TGF-β is thought to play an integral role in human bone cell physiology as a growth and/or differentiation-inducing factor (Mundy, cited supra).

In vitro, TGF-β has been shown to have strong mitogenic activity in osteoblasts (Robey et al., *J. Cell Biol.*, 105, 457 (1987)). Moreover, TGF-β is known to have multiple effects on bone-specific genes. For example, TGF-β has been shown to increase type I collagen, osteopontin, and alkaline phosphatase synthesis, and decrease osteocalcin synthesis (Noda et al., *J. Cell. Physiol.*, 133, 426 (1987); Pfeilschifter et al., *Proc. Natl. Acad. Sci USA*, 82, 2024 (1987); Wrana et al., *J. Cell Biol.*, 106, 915 (1988); Noda et al., *J. Biol. Chem.*, 263, 13916 (1988)). The regulation of these genes, as well as c-fos and jun-B (Subramaniam et al., cited supra), by TGF-β has been measured after 2–24 hours of TGF-β treatment. However, the early mechanism of action of TGF-β in bone-derived cell cultures has not been characterized.

Thus, there is a need to identify and isolate genes that are expressed immediately or very soon after exposure of bone tissues to growth factor. There is also a need to identify and isolate genes that encode factors which are involved in the regulation of bone growth and differentiation.

SUMMARY OF THE INVENTION

The present invention provides an isolated and purified DNA molecule comprising a DNA segment encoding a ribonucleic acid molecule, wherein the expression of the ribonucleic acid molecule is rapidly induced by TGF-β administration. The present invention also provides an isolated and purified DNA molecule comprising a DNA segment encoding a polypeptide, wherein the expression of the polypeptide is induced by TGF-β administration. A preferred embodiment of the invention is a DNA segment that encodes TGF-β inducible early factor-1 (TIEF-1). An isolated and purified DNA molecule comprising a DNA segment consisting essentially of SEQ ID NO:1 is also provided. These DNA molecules are double-stranded or single-stranded, preferably, they are cDNA. Another embodiment of the invention is an isolated polypeptide having an amino acid sequence corresponding to SEQ ID NO:2.

An isolated and purified DNA molecule, such as a probe or a primer, of at least seven nucleotide bases which hybridizes to these DNA molecules, or RNA molecules derived from these DNA molecules, under stringent conditions is also provided by the invention. The present invention provides a probe or a primer comprising at least seven nucleotide bases of any of the above-disclosed DNA sequences detectably labeled or having a binding site for a detectable label. Such probes or primers are useful to detect, quantify and amplify complementary DNA strands in eukaryotic tissue samples with sequences related to TIEF-1.

The present invention also provides an expression cassette comprising a DNA sequence encoding TIEF-1, operably linked to a promoter functional in a host cell. Most preferably, the DNA sequence is SEQ ID NO:1. Such expression cassettes can be placed into expression vectors which are then employed to transform prokaryotic or eukaryotic host cells. The present vectors can also contain a DNA sequence which is a selectable marker gene or reporter gene, as described below.

Also provided is a transformed host cell, the genome of which has been augmented by a recombinant DNA sequence encoding TIEF-1. Preferably, the recombinant DNA sequence is integrated into the chromosome of the transformed host cell, and is heritable.

The present invention also provides a method of introducing and expressing an exogenous TIEF-1 gene in a host cell. The method comprises introducing an expression cassette comprising a DNA sequence encoding TIEF-1 operably linked to a promoter functional in a host cell into the host cell. The DNA sequence is then expressed in the host cell. This method also provides isolated recombinant TIEF-1 protein which is recovered from the transformed host cells.

A method of identifying a growth factor or differentiation factor-inducible gene is also provided. The method comprises providing amplified cDNA from RNA isolated from cultured cells exposed to a growth factor or differentiation-inducing factor. Amplified cDNA is also provided from RNA isolated from cultured cells not exposed to the factor. Then it is determined whether a cDNA sequence is present in the cDNA from cells cultured with the factor that is not present in the cDNA from cells cultured without the factor.

As used herein, the terms "isolated and/or purified" refer to in vitro isolation of a DNA or polypeptide molecule from its natural cellular environment, and from association with other components of the cell, such as nucleic acid or protein, so that it can be sequenced, replicated, and/or expressed.

As used herein, a "recombinant" nucleic acid or polypeptide molecule or sequence is a molecule or sequence where the nucleic acid molecule or sequence which encodes the protein has been derived or isolated from any appropriate tissue or cellular source and subsequently modified in vitro, so that its sequence is not naturally occurring, or corresponds to naturally occurring sequences that are not positioned as they would be positioned in a genome which has not been transformed with exogenous DNA. An example of recombinant DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering. Therefore, "recombinant DNA" includes completely synthetic DNA sequences, semi-synthetic DNA sequences, DNA sequences isolated from biological sources, and DNA sequences derived from introduced RNA, as well as mixtures thereof.

As used herein, the term "rapidly induced" with respect to a RNA means that RNA transcription of a particular DNA in a cell is increased within about 0.01–2 hours after exposure to an agent. Preferably, the increase is between 0.5–1.5 hours after exposure.

As used herein, the term "differentially expressed" means that the expression of a particular RNA molecule is increased or decreased in a culture of cells as a result of exposure of that culture to an agent, e.g., a growth or differentiation-inducing factor, relative to a culture not exposed to the agent.

As used herein, the term "derived" with respect to a RNA molecule means that the RNA molecule has complementary sequence identity to a particular DNA molecule.

As used herein, the term "chimeric" DNA refers to a DNA comprising sequences derived from the genomes of two or more species that do not exchange DNA under normal conditions, or to DNA sequences which are linked in a manner that does not normally occur in the native genome.

As used herein, an "exogenous" DNA is DNA that has been isolated, purified, and amplified in vitro from genomic DNA, or synthetically prepared on the basis of the sequence of genomic DNA.

As used herein, the term "consisting essentially of" as used with respect to the present DNA molecules, sequences, or segments, is defined to mean that a major portion of the nucleotide sequence in the molecule, sequence or segment, encodes TIEF-1, and optionally may include DNA containing at least one marker or reporter gene, and that nucleotide sequences are not present other than those encoding TIEF-1, or optionally DNA containing marker or reporter genes.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including prokaryotic cells or insect cells.

"Transfected" or "transformed" is used herein to include any host cell or cell line, the genome of which has been altered or augmented by the presence of at least one recombinant DNA sequence, which DNA is also referred to in the art of genetic engineering as "heterologous DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding TIEF-1, which host cell may or may not express significant levels of autologous or "native" TIEF-1.

As used herein "stringent conditions" means conditions that detect a nucleic acid molecule with at least 90% nucleotide sequence homology to the probe or primer sequence. For example, stringent conditions for DNA:DNA hybridization can include hybridization conditions in 50% formamide, 2× Denhardt's, 5× SSC, 1% SDS, and 25 µg/ml RNA at 42° C. for 16 to 18 hours, followed by washing once for 5 minutes in 2× SSC at room temperature, then once for 45 minutes in 2× SSC, 1% SDS at 52° C., followed by washing once for 45 minutes at 52° C. and 0.2× SSC, 1% SDS. See Sambrook et al., *Molecular Cloning: A Laboratory Manual*, Cold Spring Harbor Laboratory Press (2nd ed., 1989) for selection of hybridization and washing conditions for DNA:DNA, as well as DNA:RNA (Northern blot), stable and specific duplex formation. For stringent conditions for Northern analysis of nucleic acids of the present invention see Lau et al., *Proc. Natl. Acad. Sci. USA*, 88, 829 (1991)).

BRIEF DESCRIPTION OF THE FIGURES

FIG. 4. cDNA sequence of TIEF-1. Nucleotide sequence (SEQ ID NO: 1) and deduced amino acid sequence (SEQ ID NO: 2) of TIEF-1 cDNA. The first "M" in the amino acid sequence denotes the translational start site. The stop codon is shown with an asterisk. The amino acids in the large boxes show the three zinc finger motifs. The proline-rich region src homology-3 (SH3) binding domains are shown in the small boxes. The underlined nucleotides indicate the polyadenylation signal sequence and AUUUA motifs. The numbers on the left denote the nucleotides and the numbers on the right refer to the amino acid residues.

FIG. 5. A diagram showing the homology of the zinc finger region of the TIEF-1 protein to other members of this family. The conserved cysteine and histidine residues in the zinc finger motif are shown in bold letters. The highly conserved amino acids in TIEF-1 and other members of this gene family are underlined. The numbers denote the amino acid positions of TIEF-1. TIEF-1=TGF-$\beta$ inducible early factor-1, SPR-2=human GT box binding protein (SEQ ID NO: 4), Sp3=human Sp3 protein (SEQ ID NO: 5), SPR-1= human GT box binding protein (SEQ ID NO: 6), Sp1= human transcription factor Sp1 (SEQ ID NO: 7), BTEB= human GC box binding protein (SEQ ID NO: 8), MUSKrp= mouse erythroid Krueppel-like transcription factor (SEQ ID NO: 9), Sp2=human Sp2 protein (SEQ ID NO: 10), and WT-1=human Wilm's tumor zinc finger protein (SEQ ID NO: 11).

Figure 6:
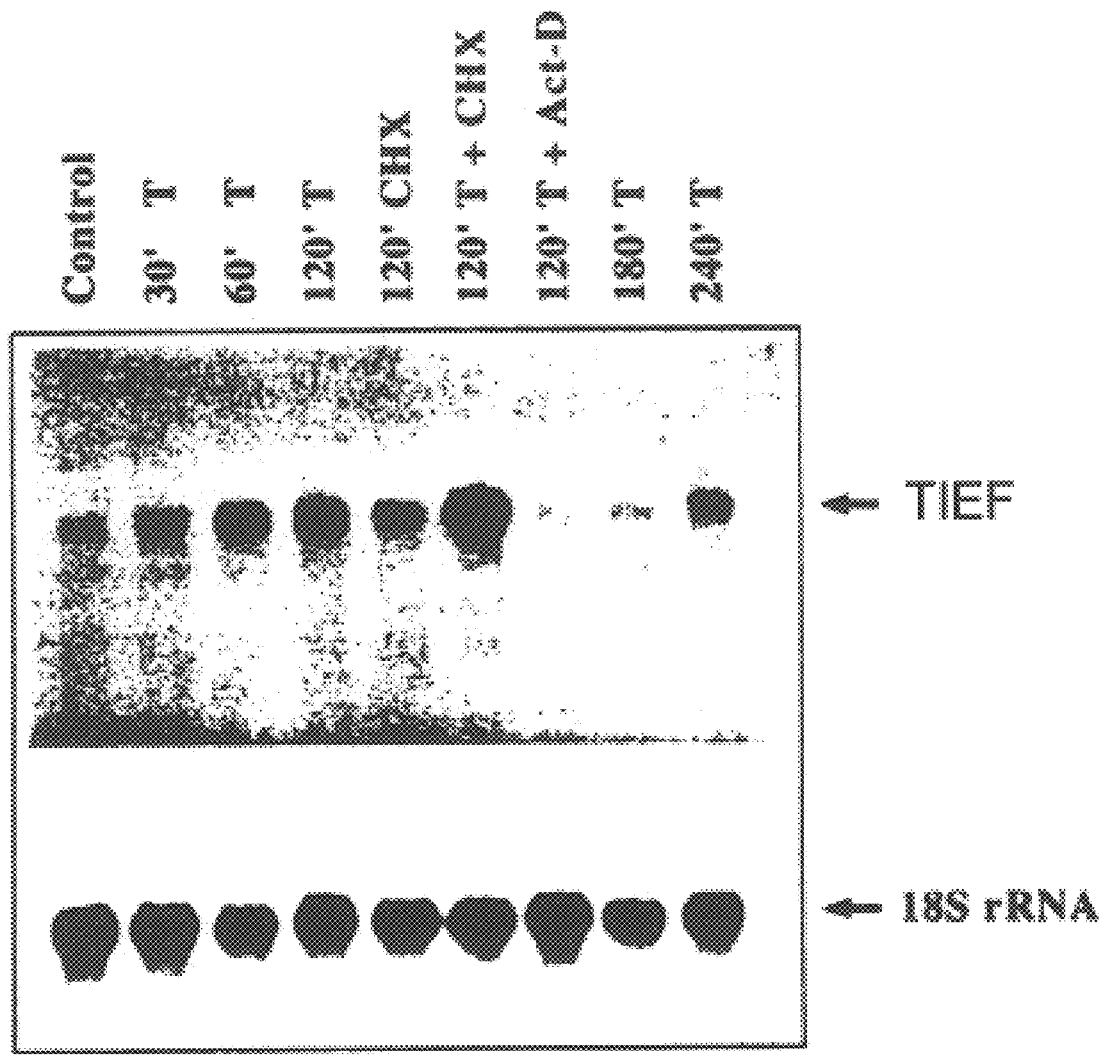

FIG. 6. Northern analyses of TIEF-1 mRNA levels after TGF-$\beta_1$, cycloheximide, and actinomycin-D treatment in hFOB cells. Serum-starved confluent hFOB cells were treated with TGF-$\beta_1$ (2 ng/ml) and/or cycloheximide (10 μg/ml) or actinomycin-D (1 μg/ml) for various time periods as indicated on top of each lane. The control cells were treated with 0.25% BSA in PBS for two hours. Total RNA was isolated from control and treated cells and 8 μg of the RNA from the cells was used for Northern analyses. The blots were probed for TIEF-1 mRNA and 18S rRNA.

Figure 7:
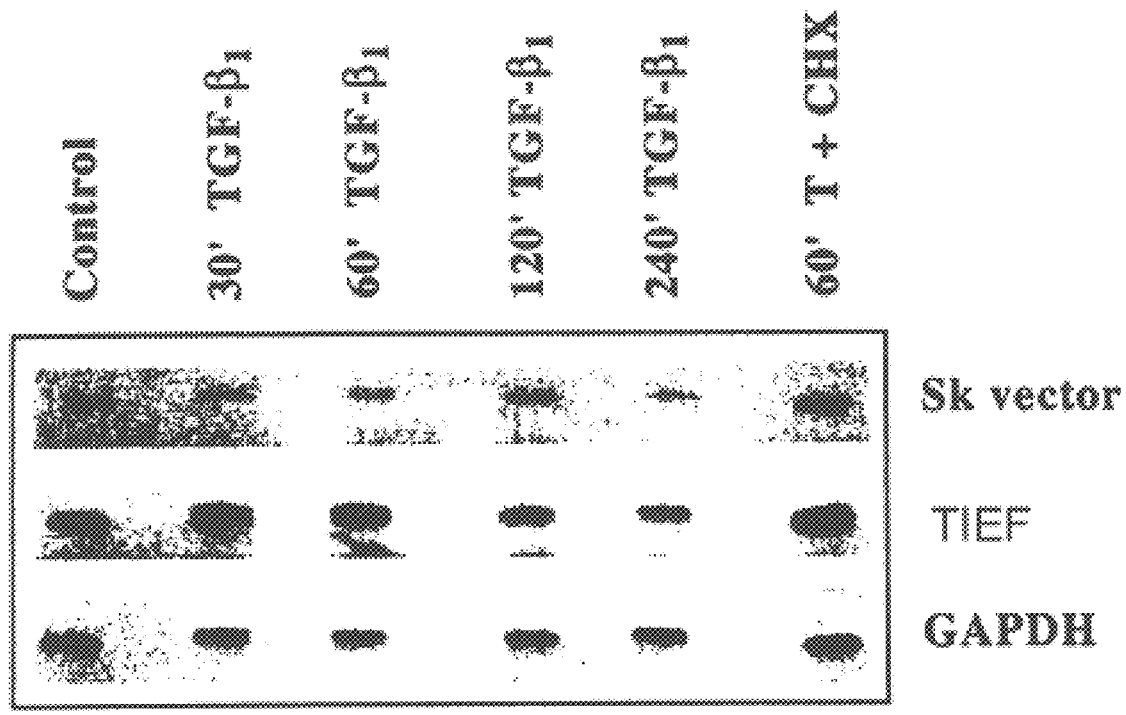

FIG. 7. Transcriptional regulation of TIEF-1 in hFOB cells. Serum-starved hFOB cells were treated with TGF-$\beta_1$ (2 ng/ml) for various time periods, nuclei were isolated, and transcripts were elongated in vitro in the presence of $^{32}$P-UTP. The labelled transcripts were hybridized to slot blotted DNA and processed for autoradiography.

Figure 8:
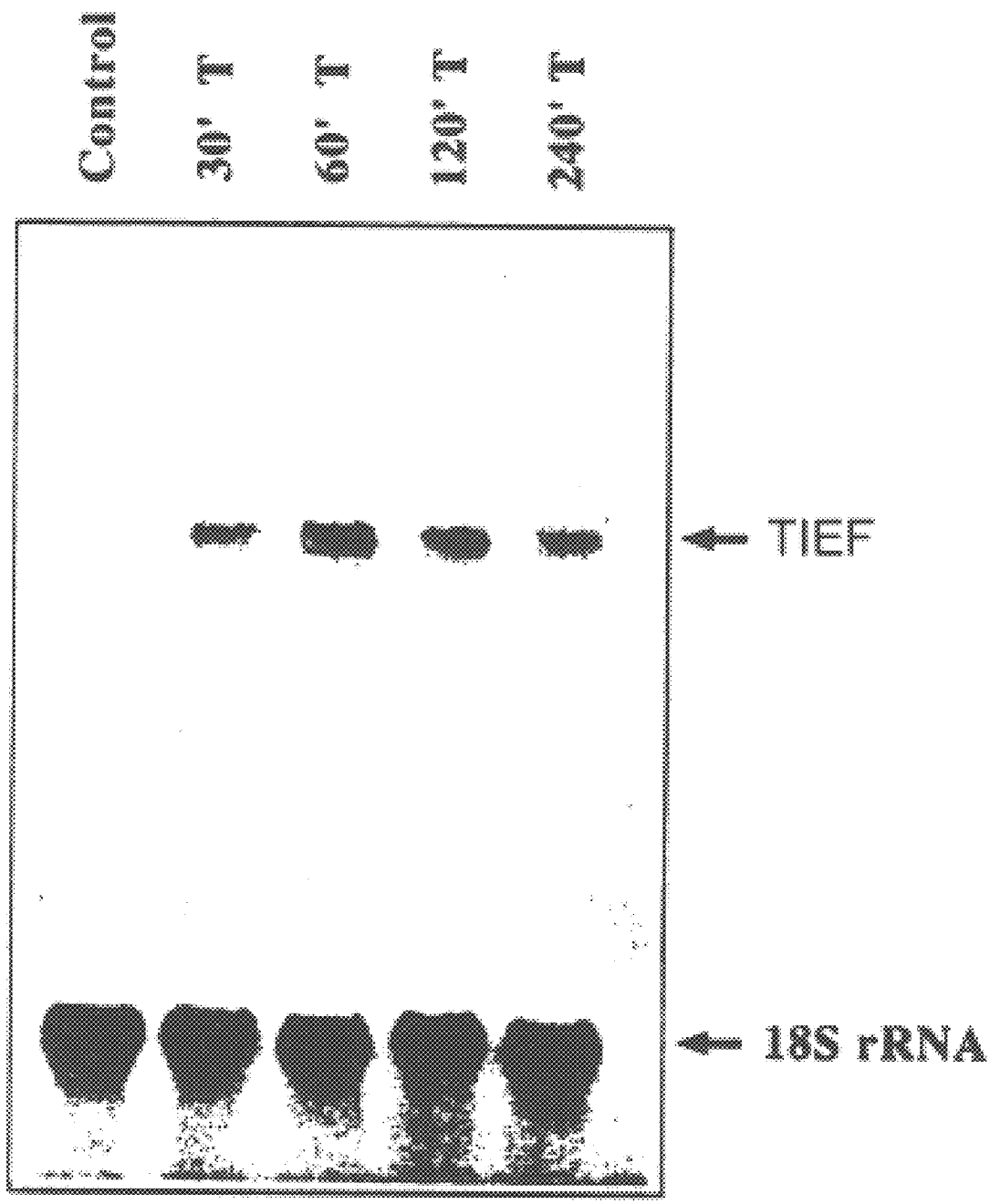

FIG. 8. Northern analyses of TIEF-1 mRNA in adult human osteoblast-like cells. Confluent adult human osteoblast-like (hOB) cells were serum-starved for 48 hours and treated with TGF-$\beta_1$ (2 ng/ml) for various time periods as shown on top of each lane. Total RNA was isolated from control (vehicle treated for two hours) and TGF-$\beta$ treated cells, and 8 μg of the RNA was used for Northern analyses. The blots were probed for TIEF-1 mRNA and 18S rRNA.

Figure 9:
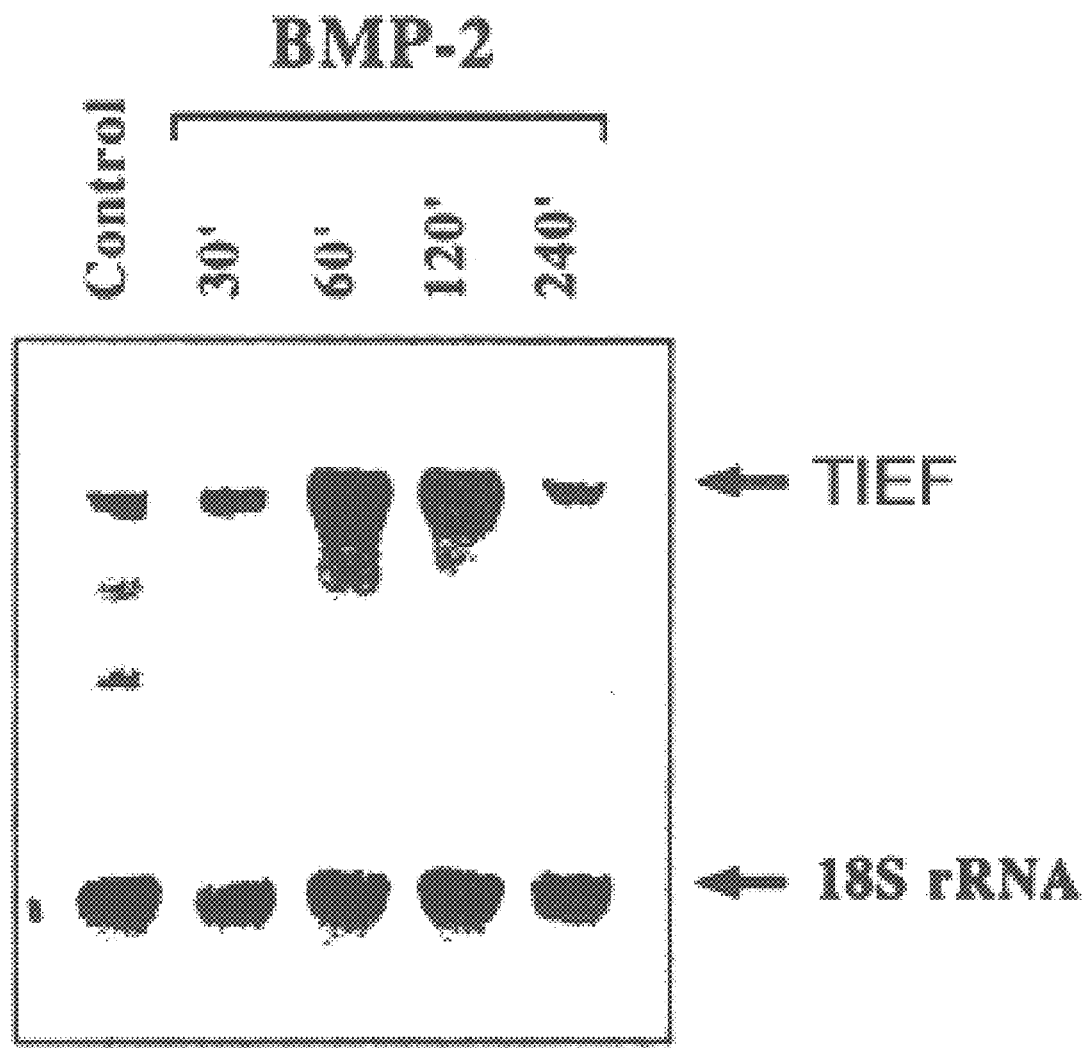

FIG. 9. Northern analyses of TIEF-1 mRNA levels after BMP-2 treatment. Confluent hFOB cells were serum-starved for 48 hours and treated with BMP-2 (100 ng/ml) for various time periods as shown on top of each lane. Total RNA was isolated from control (vehicle treated for two hours) and bone morphogenetic factor-2 (BMP-2) treated cells, and 8 μg of the RNA was used for Northern analysis. The blots were probed for TIEF-1 mRNA and 18S rRNA.

Figure 10:
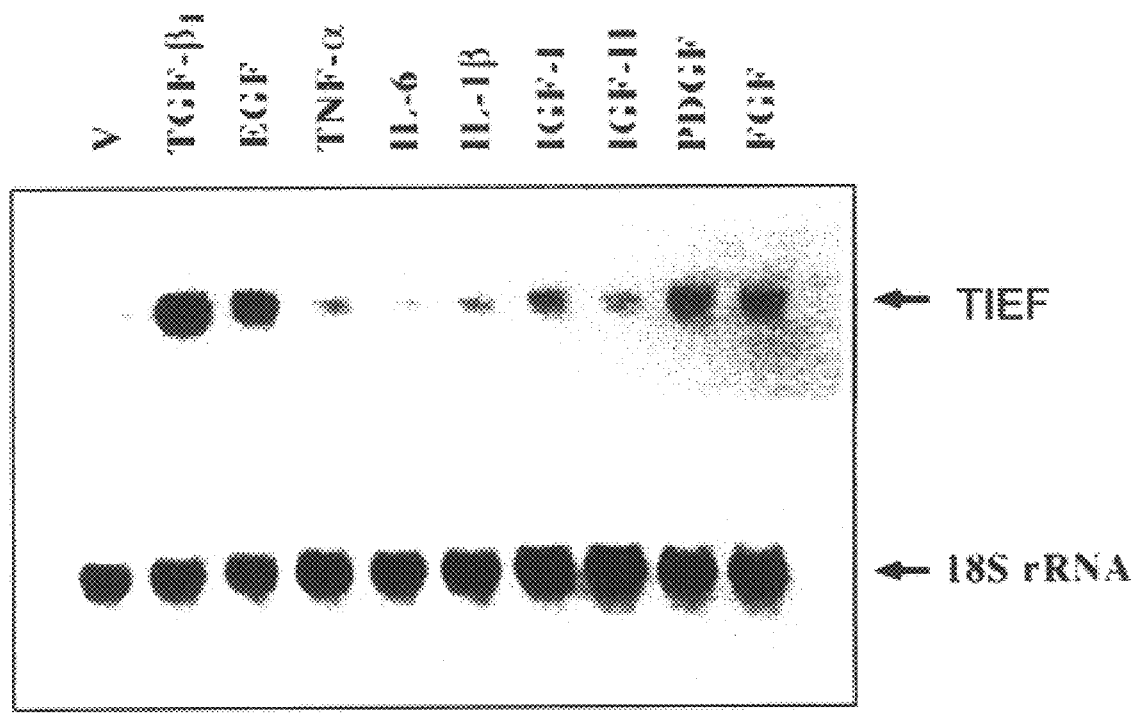

FIG. 10. Growth factor specificity of TIEF-1 expression. Serum-starved confluent hFOB cells were treated for 90 minutes with different growth factors or cytokines: TGF-$\beta_1$ (2 ng/ml), EGF (20 ng/ml), TFN-α (10 U/ml), IL-6 (10 ng/ml), IL-1β (10 U/ml), IGF-1 (3.5 ng/ml), IGF-II (3.5 ng/ml), PDGF 5 ng/ml), and FGF (10 ng/ml). Total RNA was isolated from vehicle-treated (0.25% BSA in PBS for 90 minutes) and growth factor-treated cells and 10 μg of the total RNA was used for Northern analyses. The blots were probed for TIEF-1 mRNA and 18S rRNA.

Figure 11:
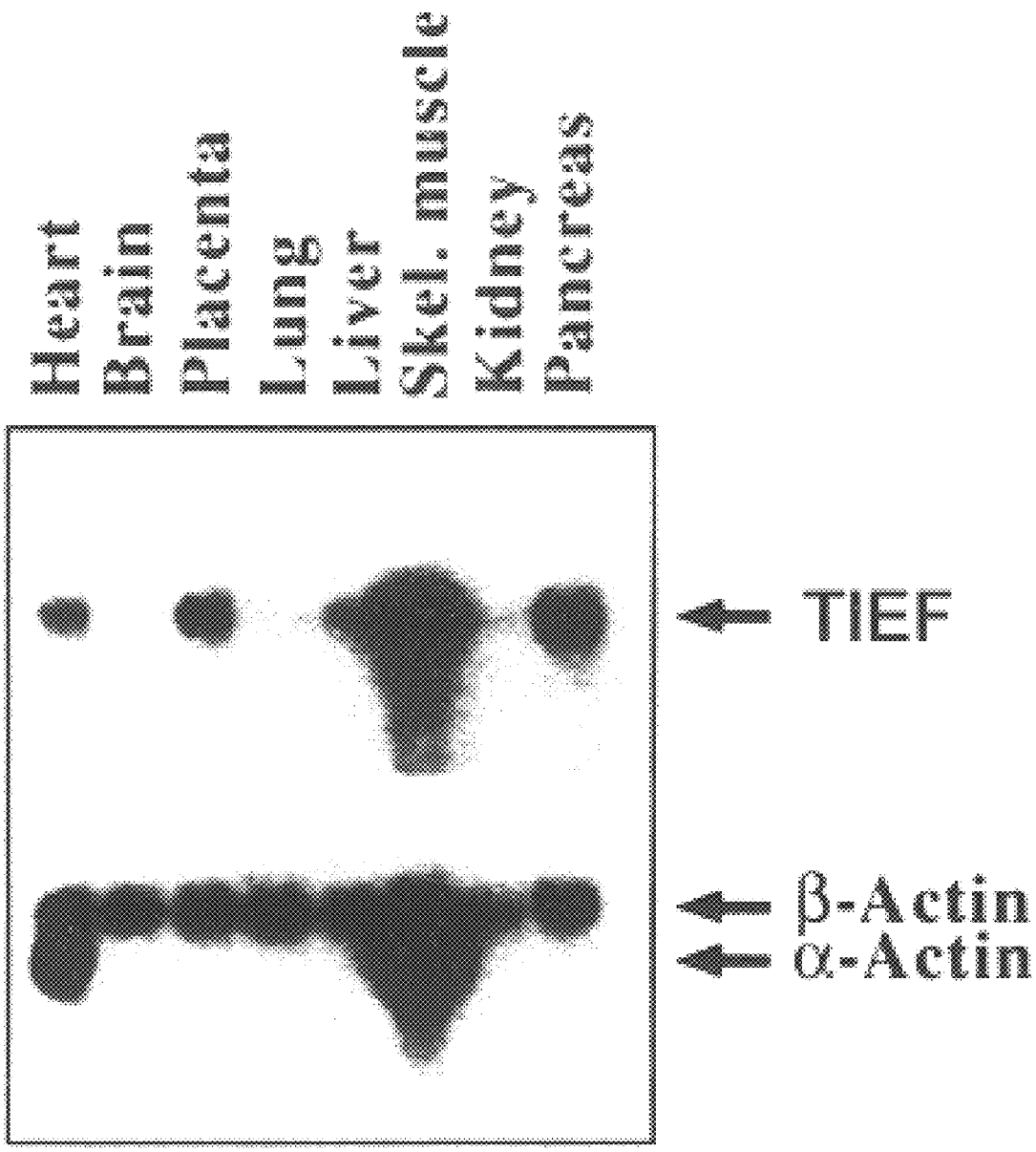

FIG. 11. Tissue specificity of TIEF-1 expression. Multi-tissue Northern blot containing 2 μg of poly A$^+$ RNA (purchased from Clontech, Palo Alto, Calif.) isolated from the indicated tissues. The blot was probed with TIEF-1 cDNA and human β-actin cDNA.

DETAILED DESCRIPTION OF THE INVENTION

In order to more fully understand the mechanism by which TGF-β influences bone cell metabolism, and to identify and molecularly characterize the factor(s) which are expressed by bone tissue immediately or very early after exposure to growth factors, such as TGF-β or EGF, cDNAs from growth factor stimulated bone cells were generated by the differential display PCR technique described by Liang et al. (Science, 257, 967 (1992) and *Nucl. Acids Res.*, 21, 3269 (1993)).

Besides identifying factors which may play a role in bone tissue growth and differentiation, the identification and isolation of DNAs encoding factor(s) which are differentially expressed after growth factor administration may be useful for defining the molecular basis for bone pathologies, for providing a clinically useful diagnostic test, or in molecular-based therapeutics. Once such a factor has been identified, an antibody specific for the factor can be made. Patient sera or plasma can then be incubated with the antibody to determine if the factor is present in the patient in an amount different than that found in patients without a bone disease or pathology. Furthermore, the cloning of the gene encoding the factor will elucidate the molecular mechanism giving rise to the presence of this factor in patients with an alteration in bone physiology or during periods of normal bone growth and differentiation. Once the molecular mechanism underlying the expression of the gene is understood, molecular genetic-based therapies directed to controlling the expression of this gene can then be employed to correct or supplement the expression of the gene in patients with bone abnormalities.

Factors differentially expressed immediately or very early after growth factor administration are also useful to clarify the role that these factors play in the growth and differentiation of other tissues, such as skeletal muscle, heart, placenta, and pancreas.

Specifically, the present invention provides an isolated and purified DNA molecule comprising a cDNA sequence such as that represented by the complete nucleotide sequence shown in FIG. 4 (SEQ ID NO:1), which comprises a DNA segment encoding TGF-β inducible early factor-1 (TIEF-1). The present invention further provides an isolated amino acid sequence comprising the amino acid sequence shown in FIG. 4 (SEQ ID NO:2).

The probes and primers of the present invention are useful for detecting the expression of the DNA molecules of the present invention, and amplifying nucleic acid sequences that fall within the scope of the present invention. The uses of probes and primers, as well as their isolation, purification and conditions under which they are employed for the detection or amplification of a specific gene, are well known in the art.

The present invention also provides isolated and purified DNA molecules which provide "anti-sense" mRNA transcripts of the DNA sequences shown in FIG. 4 which, when expressed from an expression vector in a host cell, can alter bone tissue growth and differentiation.

The polymorphic cDNA sequences of the present invention can be introduced into the genome of a host cell, including, but not limited to, mammalian, bacterial, or insect cells, by in vitro techniques known in the art, to yield a transformed cell having the cDNA stably integrated into its genome, so that the DNA molecules, sequences, or segments, of the present invention are expressed by the host cell. That is, the present invention also provides a transformed host cell having a genome augmented by a recombinant (non-native) DNA sequence, preferably by a chromosomally integrated recombinant (genetically engineered) DNA sequence that includes a gene encoding for TIEF-1.

The recombinant DNA sequence, used for transformation herein, may be circular or linear, double-stranded or single-stranded. Generally, the DNA sequence is in the form of chimeric DNA, such as plasmid DNA, that can also contain coding regions flanked by regulatory sequences which promote the expression of the recombinant DNA present in the resultant cell line. For example, the recombinant DNA may itself comprise a promoter that is active in mammalian cells, or may utilize a promoter already present in the genome that is the transformation target. Promoters useful for this purpose in eukaryotic host cells include, but are not limited to, the CMV promoter, as well as the SV 40 late promoter and retroviral LTRs (long terminal repeat elements).

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

Moreover, the general methods for isolating and purifying a recombinantly expressed protein from a host cell are well known to those in the art. Examples of the isolation and purification of such proteins are given in Sambrook et al., cited supra.

Aside from recombinant DNA sequences that serve as transcription units for TIEF-1 or portions thereof, a portion of the recombinant DNA may be untranscribed, serving a regulatory or a structural function. The recombinant DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in host cells. Useful selectable markers are well known in the art and include, for example, antibiotic and herbicide-resistance genes, such as neo, hpt, dhfr, bar, aroA, dapA, and the like.

Reporter genes are used for identifying potentially transformed cells and for evaluating the functionality of regulatory sequences. Reporter genes which encode for easily assayable marker proteins are well known in the art. In general, a reporter gene is a gene which is not present in or expressed by the recipient organism or tissue and which encodes a protein whose expression is manifested by some easily detectable property, e.g., enzymatic activity. Preferred genes for the transformation processes of the present invention include the chloramphenicol acetyl transferase gene (cat) from Tn9 of *E. coli*, the beta-galactosidase gene of *E. coli*, and the luciferase gene from firefly *Photinus pyralis*. Expression of the reporter gene is assayed at a suitable time after the DNA has been introduced into the recipient cells.

Other elements such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The recombinant DNA can be readily introduced into the target cells by transfection with an expression vector comprising a cDNA encoding TIEF-1 by any procedure useful for the introduction into a particular cell, e.g., calcium phosphate precipitation, lipofection, electroporation, and the like.

Sources of nucleotide sequences useful in the present invention include total or polyA+ RNA from mammalian osteoblastic, osteoclastic, or muscle skeletal cells, as well as RNA isolated from tissue samples of bone, skeletal muscle, heart, pancreas, placenta and the like, from which the cDNA encoding TIEF-1 can be derived by methods known in the art.

The present invention also provides purified, isolated TIEF-1 protein, which can be prepared by recombinant DNA methodologies as disclosed hereinbelow. However, since the present invention provides the amino acid sequence of human TIEF-1 (FIG. 4), TIEF-1 or bioactive analogs thereof can also be synthesized by the solid phase peptide synthetic method. This established and widely used method, including the experimental procedures, is described in the following references: Stewart et al., *Solid Phase Peptide Synthesis*, W.H. Freeman Co., San Francisco (1969); Merrifield, *J. Am. Chem. Soc.*, 85, 2149 (1963); Meienhofer in "Hormonal Proteins and Peptides," ed.; C. H. Li, Vol. 2 (Academic Press, 1973), pp. 48–267; and Bavaay and Merrifield, "The Peptides," eds. E. Gross and F. Meienhofer, Vol. 2 (Academic Press, 1980) pp. 3–285.

The invention has been described with reference to various specific and preferred embodiments and will be further described by reference to the following detailed examples. It is understood, however, that there are many extensive variations, and modifications on the basic theme of the present invention beyond that shown in the examples and description, which are within the spirit and scope of the present invention.

EXAMPLE 1

Materials and Methods

Cell Culture and RNA isolation. The immortalized human fetal osteoblastic (hFOB) cell line, hFOB 1.19, was recently described by Harris et al. (*J. Bone Miner. Res.*, 10, 178 (1995)). The hFOB cells were routinely grown in DMEM:F12 (1:1) with 10% FBS serum containing media. Cells were plated onto 100 mm culture dishes and allowed to grow to near confluency. At this time, the cells were washed twice with serum-free media and incubated in 10 ml of 1% serum containing media for 48 hours. The serum starved cells were treated with TGF-$\beta_1$ (2 ng/ml) for different time periods and the cells were processed for total RNA isolation using the guanidinium/cesium chloride method of Chirgwin et al. (*Biochemistry*, 18, 5294 (1979)).

Primary cultures of normal adult human osteoblasts (hOB) were grown in culture as described above and the cells were treated with TGF-$\beta_1$ for various time periods and Northern analyses were performed as described below. Northern blot analysis. Northern blot analysis was performed essentially as described in Subramaniam et al., *J. Cell. Biochem.*, 57, 52 (1995). Briefly, 8 to 15 µg of total RNA preparations were denatured and resolved in a 1% glyoxal agarose gel during electrophoresis. The RNAs were transferred overnight to a Magna 66 nylon membrane (MSI, Fischer Scientific, Pittsburgh, Pa.) by capillary action in 20× SSC (3 M NaCl, 0.3 M trisodium citrate, pH 7.0). The filters were baked for 2 hours at 80° C., hybridized with a [$^{32}$P]-labelled probe, and the blots washed as previously described (Lau et al., *Proc. Natl. Acad. Sci. USA*, 88, 829 (1991)). The probes were labelled with $^{32}$P by random primer extension using the Multiprime DNA labelling system (NEN Research Products, Boston, Mass.). [α-$^{32}$P]dCTP with a specific activity of approximately 3000 Ci/mmol (NEN Research Products, Boston, Mass.) was used radiolabel the DNA probes to achieve specific activities of approximately $10^9$ cpm/mg.

Differential Display PCR. Differential display PCR (Liang and Pardee and Liang et al. (both cited supra)) was performed following the manufacturer's protocol (GenHunter kit, Brookline, Mass.). Total RNA was isolated from hFOB 1.19 cells that had been treated with either vehicle (0.25% BSA in PBS) or $10^{-8}$ M TGF-$\beta_1$ for 60 minutes using the guanidinium/cesium chloride method of Chirgwin et al. (cited supra). Total RNA was treated with RNAse-free DNAse to remove any DNA contamination. DNA-free RNA (0.2 µg) from control and TGF-$\beta_1$-treated cells was used as a template for first strand cDNA synthesis in the presence of 10 µM $T_{12}$ MG, $T_{12}$ MC, $T_{12}$ MA, and $T_{12}$ MT primers, MMLV-reverse transcriptase, reverse transcriptase buffer, and 250 µM dNTP mix. $T_{12}$ MG, $T_{12}$ MC, $T_{12}$ MA, $T_{12}$ MT, and $T_{12}$ MN are degenerate anchored oligo-dT primers. For example, $T_{12}$ MA has twelve dT nucleotides followed by either a dG, dA or dC nucleotide which is followed by a dA nucleotide. $T_{12}$ MN has twelve dT nucleotides followed by either a dG, dA or dC nucleotide followed by any of the four deoxyribonucleotides. The synthesized first strand cDNA was used as a template in the next PCR reaction.

In a 0.5 ml microfuge tube the following were added: 2 µl of 10×PCR buffer (50 mM KCl, 1.5 mM MgCl$_2$, 10 mM Tris-HCl, pH 8.3), dNTP mix (25 µM), 5'-random primer (2 µM), $T_{12}$ MN mix (the same used in the cDNA synthesis described above), 1 µCi of dCTP (3000 Ci/mmol), 2 µl of template cDNA and 1 unit of Taq DNA polymerase (Perkin Elmer). PCR was performed as follows: 94° C., 30 seconds; 40° C., 2 minutes; 72° C., 30 seconds; for 40 cycles. After the PCR was completed, 6 µl of the sample was run on a 6% urea:acrylamide sequencing gel. The dried gel was exposed to an x-ray film and the autoradiogram was analyzed for the differentially expressed genes. After identifying a differentially expressed band from the autoradiogram of ca. 350 bp in size, the gel was superimposed over the autoradiogram and the band was cut out.

The DNA in the band was then eluted from the gel by soaking the gel in a 100 µl of TE buffer for 10 minutes and then boiling the gel in TE buffer for 10 minutes. The DNA was precipitated using glycogen and ethanol. The precipitated DNA was dissolved in a small volume of dH$_2$0. A portion of this DNA was used as a template in the second PCR along with the same 5' and 3' primers used in the first PCR. The amplified DNA obtained was analyzed in a 1.5% agarose gel. Once the DNA was found to be pure, i.e., without any other contaminating DNA bands, dNTPs and proteins were removed. This DNA was then used as a probe in Northern analyses and cDNA library screening. cDNA Library Screening. To obtain the full length TIEF-1 cDNA, a hOB cDNA library was screened using the 350 bp DNA fragment described above which represents the 3'-end of the TIEF-1 cDNA. The hOB cDNA library was kindly provided by Dr. Marian Young at the National Institutes of Health. The cDNA library was constructed using poly A$^+$ RNA obtained from a 55 year-old female who had hip replacement surgery. Using the 350 bp DNA as a probe, ~200,000–400,000 plaques were screened. In the primary screen, three positive clones were obtained. The three clones were plated for a secondary screen, but only one of the clones was a potential positive clone. The tertiary screen confirmed this, since 100% of the plaques were positive.

Since the cDNA library was constructed in a lambda ZAPII vector, a pBluescript plasmid containing the insert could be obtained by the in vivo excision of the plasmid from lambda ZAPII vector. The pBluescript plasmid containing the insert was digested with EcoRI to liberate the cDNA insert from the vector. A 2.9 kb insert was obtained. Both strands of the 2.9 kb cDNA were then completely sequenced using a PCR-based sequencing kit and an automated sequencer. There was perfect homology between the 350 bp DNA fragment obtained after differential display PCR and the 3'-end of the 2.9 kb cDNA. The 2.9 kb DNA sequence was analyzed for homologies with known genes in the Genbank using University of Wisconsin GCG Program Fast A.

Results

Figure 1:
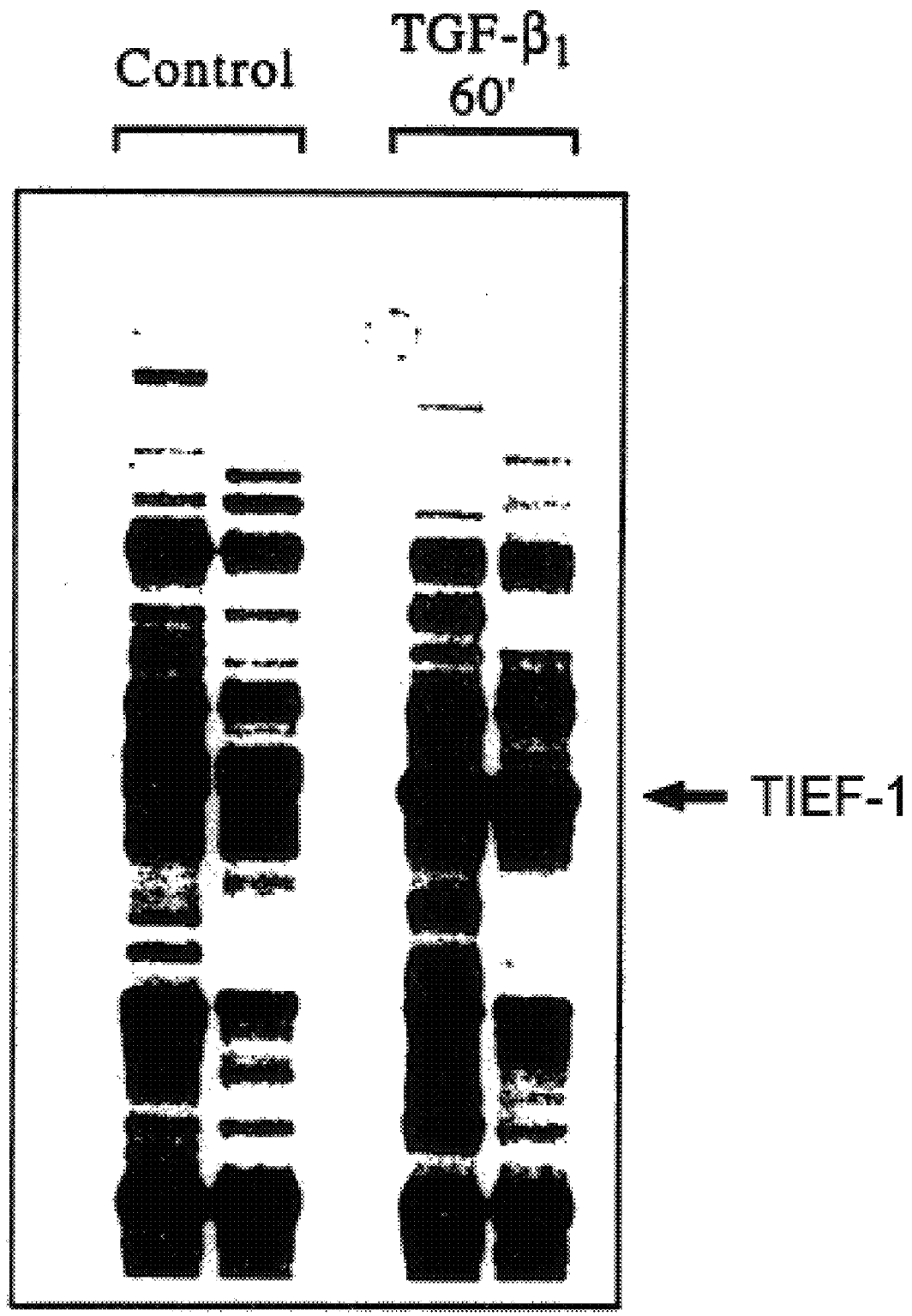
FIG. 1. Differential display PCR analysis. Near confluent human fetal osteoblastic (hFOB) cells were serum-starved with DMEM+F12 media containing 1% fetal bovine serum (FBS) for 48 hours. The serum-starved cells were stimulated with TGF-$\beta_1$ (2 ng/ml) for 60 minutes and the control cells were treated with 0.25% bovine serum albumin (BSA) in phosphate-buffered saline (PBS) for 60 minutes. Total RNA was isolated from control and treated cells. The RNA was treated with DNAse to remove any DNA contamination and 0.2 µg was used in cDNA synthesis in the presence of $T_{12}$ MN primer mix (GenHunter kit, Brookline, Mass.) and MMLV-reverse transcriptase. A portion of the cDNA in the presence of $T_{12}$ MN mix (as a 3' primer), 5'-CCTGTAATCC-3' (SEQ ID NO: 3, as a 5' primer), [$^{32}$P]-dCTP and a dNTP mix was PCR amplified and the products were analyzed in a 6% urea-acrylamide gel. Samples from each lane were obtained from independent PCR reactions from different RNA samples. The gel was dried and exposed to an x-ray film.
Figure 2:
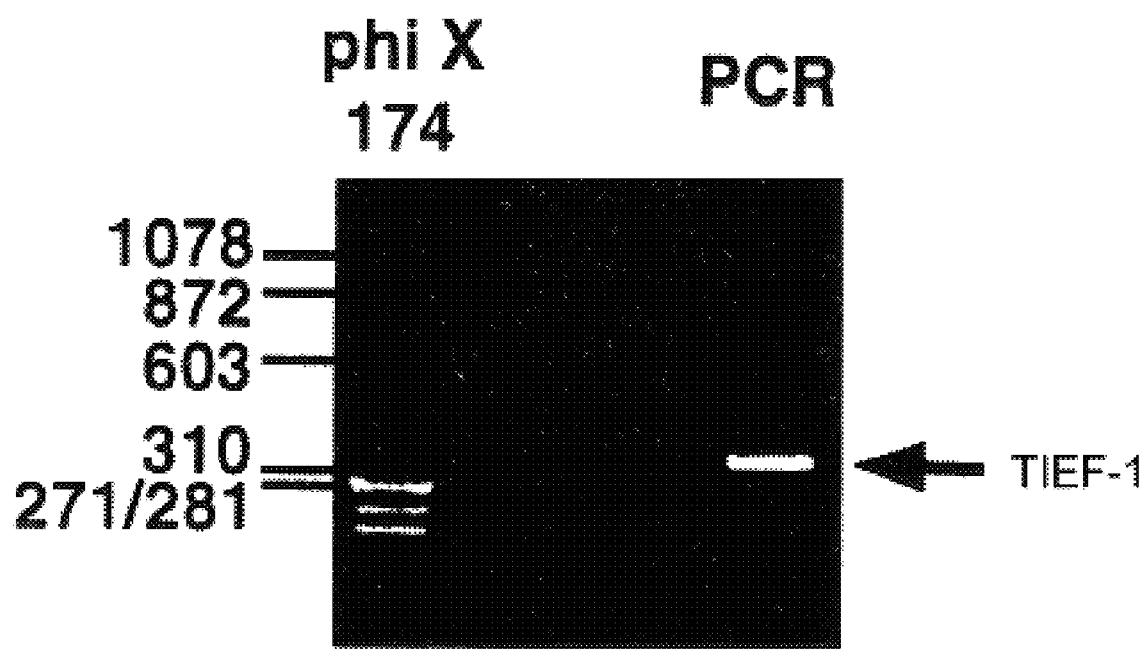
FIG. 2. Differentially displayed cDNA was PCR amplified and 500 ng of the DNA was separated on a 1.5% agarose gel along with DNA size markers.

When differential display PCR was performed from hFOB cell RNA, a 350 bp TGF-$\beta$ inducible early gene cDNA fragment (350 bp TIEF-1 cDNA) was highly expressed in hFOB cells which were treated with TGF-$\beta$ for 60 minutes compared to control (untreated) cells (FIG. 1). The cDNA fragment was purified from a sequencing gel and used as a probe for Northern analyses.

Figure 3:
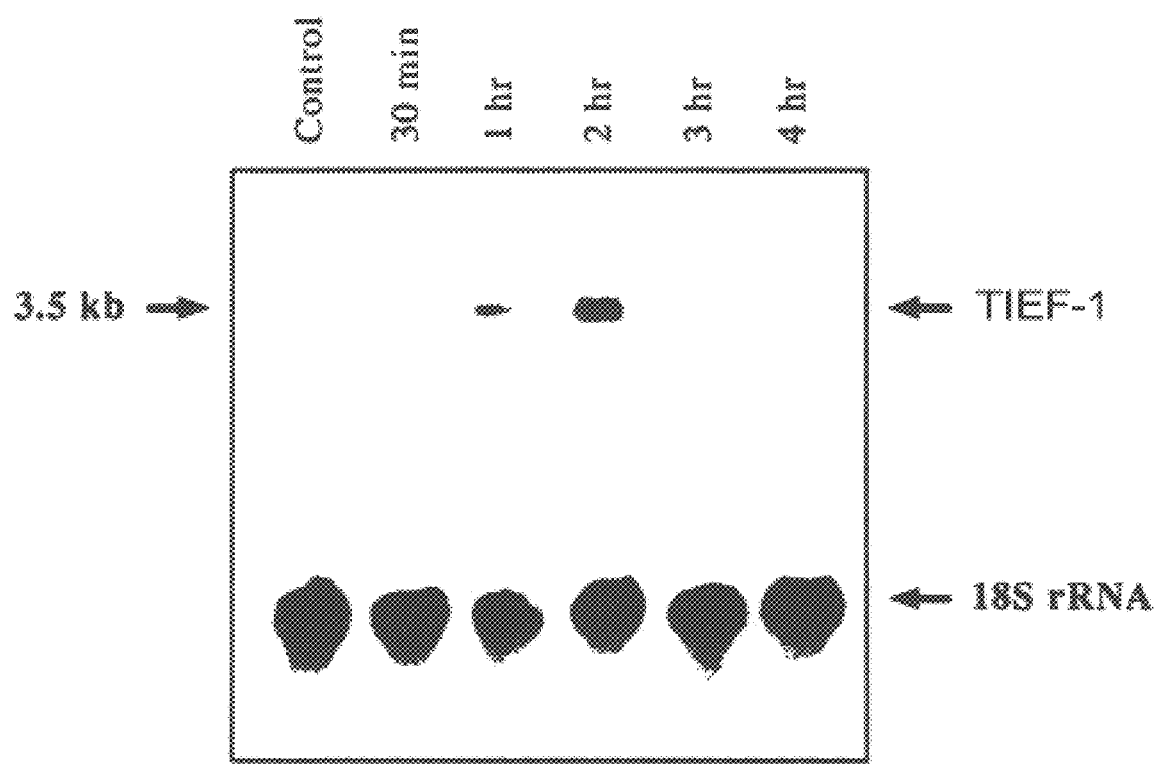
FIG. 3. Northern analyses of TIEF-1 RNA in hFOB cells. hFOB cells were serum-starved in 1% serum containing media for 48 hours. The serum-starved cells were treated with TGF-$\beta_1$ for various time periods as shown on top of each lane. Total RNA was isolated and 15 µg of RNA from each time point was used for Northern analysis. The differentially displayed cDNA from TGF-$\beta_1$-treated cells was used as a probe for the Northern blot.

RNA was isolated from hFOB cells, treated with TGF-$\beta_1$ for various time periods, fractionated on glyoxal agarose gels, and probed with the 350 bp TIEF-1 cDNA. The differentially expressed TIEF-1 mRNA was minimally detectable in control (vehicle treated) cells, but a rapid and transient increase was observed at 30 minutes after addition of TGF-$\beta_1$. There was a maximal (greater than 10-fold above control) level of expression measured at two hours post-treatment. The steady state levels of this 3.5 kb mRNA returned to control levels following three hours of TGF-$\beta_1$ treatment (FIG. 3).

To obtain the full length cDNA, a normal human osteoblast-like cell cDNA library was screened using the 350 bp TIEF-1 cDNA. The library screening resulted in the isolation of a 2.9 kb cDNA encoding a 480 amino acid residue protein, having a long 3'-untranslated region. The cDNA sequence (SEQ ID NO:1) and predicted amino acid sequence (SEQ ID NO:2) are shown in FIG. 4. The amino acid sequences in TIEF-1 which contain the highly conserved zinc finger motifs, as well as other conserved amino acid residues, are shown in FIG. 5.

To determine whether the induction of TIEF-1 RNA by TGF-$\beta$ is dependent on new protein synthesis, hFOB cells were treated with TGF-$\beta_1$ together with the protein synthesis inhibitor, cycloheximide (10 µg/ml for two hours), and Northern analyses performed using the labelled full length cDNA. A super-induction of TIEF-1 mRNA was observed at two hours post-treatment (FIG. 6). This strongly suggests that the increase in TIEF-1 mRNA in hFOB by TGF-$\beta$ is a primary response and is independent of new protein synthesis. The control of TIEF-1 mRNA expression could also be under the negative control of a protein repressor.

It is also possible that cycloheximide inhibits nucleases that are involved in degradation of TIEF-1 mRNA. This possibility is supported by the fact that TIEF-1 mRNA contains three AUUUA motifs in the 3'-untranslated region of TIEF-1, motifs which are found in c-fos and c-myc nuclear proto-oncogene mRNAs. This motif is a signal for rapid mRNA degradation (Schiavi et al., *Biochimica et Biophysica Acta*, 1114, 95 (1992)). As shown in FIG. 6, the TIEF-1 mRNA returns to near control levels at 3–4 hours after the addition of TGF-$\beta$.

When the RNA synthesis inhibitor actinomycin-D (1 µg/ml), was included with TGF-$\beta$ for the same period of time, the increase in TIEF-1 mRNA was inhibited (FIG. 6). These results suggest that the induction of TIEF-1 mRNA by TGF-$\beta$ is mediated, at least in part, at the level of transcription. In fact, nuclear run-on transcriptional analysis indicates that the TGF-$\beta$ regulation of TIEF-1 expression occurs at the level of transcription (FIG. 7).

To determine whether TIEF-1 expression is regulated by TGF-$\beta$ in normal adult osteoblastic cells, hOB cells were treated for various time periods and Northern analyses performed (FIG. 8). These data show that a progressive increase in TIEF-1 mRNA is observed with a maximal increase at 1–2 hours of TGF-β treatment.

To determine whether other members of TGF-β superfamily have any effect on TIEF-1 mRNA levels, hFOB cells were treated with bone morphogenetic protein-2 (BMP-2) at a concentration of 100 ng/ml for various time periods, and analyzed by Northern analysis. FIG. 9 shows that the TIEF-1 mRNA levels increased at 1–2 hours of BMP-2 treatment. These data indicate that other members of the TGF-β family also regulate the expression of TIEF-1 in these cells.

To determine if the induction of TIEF-1 mRNA in hFOB cells is specific to the TGF-β family of growth factors, cells were treated with different growth factors and cytokines, such as EGF, PDGF, IGF's, FGF, TNF-α, IL-6, and IL-1β. The results of this study are shown in FIG. 10. It is evident that TGF-β is the major inducer of TIEF-1 mRNA levels, with a lesser effect by EGF. The remaining growth factors/cytokines had only a minimal effect on TIEF-1 expression.

To investigate whether TIEF-1 expression is specific to osteoblasts or is expressed in other human tissues, multi-tissue Northern analysis was performed. The Northern blot contained an equal amount of poly A$^+$ RNA from different human tissues which was normalized to β-actin mRNA levels. The blot was probed with TIEF-1 cDNA, and the results are shown in FIG. 11. Skeletal muscle showed the highest level of TIEF-1 mRNA relative to β-actin. Heart, placenta, and pancreas had moderate amounts of TIEF-1 mRNA, while liver tissue showed minimal expression of this gene. Other tissues, e.g., brain, lung, and kidney had no detectable levels of the TIEF-1 mRNA. As expected, both heart and skeletal muscle showed expression of α-actin mRNA in addition to β-actin. The above results demonstrate a partial tissue specificity of TIEF-1 expression.

Discussion

A novel TGF-β inducible early gene (TIEF-1) in human osteoblasts has been identified. The regulation of this gene occurs as early as 30 minutes after TGF-β treatment and is independent of new protein synthesis. The induction of TIEF-1 mRNA in hFOB cells was restricted to the growth factors TGF-β and EGF. TIEF-1 mRNA levels in hFOB cells were also induced by BMP-2, a member of the TGF-β superfamily.

TIEF-1 mRNA levels show a tissue specificity, with osteoblast and muscle cells displaying the highest levels of mRNA expression. Since these cells arise from common progenitor cells in marrow stroma, as well as the fact that TGF-β and BMP-2 are involved in osteoblast growth and differentiation (Mundy, cited supra), TIEF-1 may be involved in osteoblast function or the function of cells in the osteoblast lineage. Thus, it is possible that this early regulated gene represents a key regulatory factor involved in the action of the general TGF-β family members on target cells.

The cDNA sequence analyses of TIEF-1 indicated that this gene contains three zinc finger motifs at the C-terminal region of the protein. This region of the protein is homologous to zinc finger-containing transcription factors like Sp1, Sp3, Wilm's tumor protein, GT box binding protein, and other zinc finger proteins. In contrast, the N-terminal region of the protein was found to be unique showing no homology to any genes in the Genbank. The zinc finger containing domains were first identified in Xenopus transcription factor TFIIIA (Miller et al., *EMBO J.*, 4, 1609 (1985)) and are known to bind nucleic acid (reviewed in Klug et al., *TIBS*, 12, 464 (1987); Berg, *Proc. Natl. Acad. Sci. USA*, 85, 99 (1988)).

The transcription factor CTF/NF-1 is known to contain proline-rich domains in the C-terminal region which are responsible for a transcriptional activating function (Mermod et al., *Cell*, 58, 741 (1989)). Interestingly, the C-terminal region of TIEF-1 contains a similar proline-rich region (24% proline residues within 125 amino acids) analogous to that of CTF/NF-1 transcription factors. Proline-rich regions are known to bind Src homology-3 (SH3) domains (Ren et al., *Science*, 259, 1157 (1993)). Yu et al. (*Cell*, 76, 933 (1994)) have reported a proline motif of PXXP that can bind SH3 domains which are highly conserved among numerous proteins. The C-terminal region of TIEF-1 contains four PXXP motifs. These proline motifs in TIEF-1 may associate with SH3 domains of src tyrosine kinases which may be involved in the signal transduction processes.

Because TIEF-1 mRNA is rapidly, but transiently, induced in osteoblastic cells following TGF-β treatment, it may be an important early signalling molecule for TGF-β. Therefore, the TIEF-1 gene may represent a key regulatory gene which mediates the effects of TGF-β on target cell (i.e., osteoblast) growth and function.

The complete disclosure of all patents, patent documents and publications cited herein are incorporated by reference as if individually incorporated. The foregoing detailed description and examples have been given for clarity of understanding only. No unnecessary limitations are to be understood therefrom. The invention is not limited to the exact details shown and described for variations obvious to one skilled in the art will be included within the invention defined by the claims.

What is claimed is:

1. A method of introducing and expressing a DNA sequence encoding a mammalian polypeptide having three zinc finger domains in a host cell, comprising:
   (a) introducing into a host cell a recombinant DNA comprising an expression cassette consisting of a DNA sequence operably linked to a promoter functional in the host cell, wherein the DNA sequence encodes a mammalian polypeptide having three zinc finger domains, and wherein the DNA sequence encodes the polypeptide of SEQ ID NO:2; and
   (b) expressing the DNA sequence in the host cell so as to yield the mammalian polypeptide.

2. The method of claim 1 further comprising isolating the polypeptide expressed from the DNA sequence.

3. The method of claim 1 wherein the DNA sequence comprises SEQ ID NO:1.

4. The method of claim 3 wherein the DNA sequence consists of SEQ ID NO:1.

5. An isolated and purified DNA molecule consisting of a DNA segment encoding a polypeptide having three zinc finger domains, wherein the DNA segment encodes the polypeptide of SEQ ID NO:2.

6. The isolated and purified DNA molecule of claim 5 wherein expression of the DNA segment is induced by TGF-β in bone cells.

7. The isolated DNA molecule of claim 5 wherein the DNA segment comprises SEQ ID NO:1.

8. The isolated DNA molecule of claim 7 wherein the DNA segment consists of SEQ ID NO:1.

9. An isolated and purified DNA molecule consisting of a DNA segment comprising SEQ ID NO:1 or a DNA molecule complementary thereto, which complementary DNA molecule has a nucleotide sequence that is identical to the complement of SEQ ID NO:1.

10. An isolated and purified DNA molecule of at least seven nucleotide bases which specifically hybridizes to the DNA molecule of claim 9.

11. A hybridization probe comprising an isolated and purified DNA sequence of at least seven nucleotide bases, which is detectably labeled or which binds to a detectable label, which DNA sequence specifically hybridizes under stringent conditions to a RNA molecule derived from the DNA molecule of claim 9, or specifically hybridizes under stringent conditions to the DNA molecule of claim 9.

12. An expression cassette consisting of a DNA sequence encoding a polypeptide operably linked to a promoter functional in a host cell, wherein the polypeptide has three zinc finger domains, and wherein the DNA sequence encodes the polypeptide of SEQ ID NO:2.

13. The expression cassette of claim 12 wherein the DNA sequence comprises SEQ ID NO:1.

14. The expression cassette of claim 12 wherein the DNA sequence consists of SEQ ID NO:1.

15. A host cell, the genome of which has been modified by a recombinant DNA comprising an expression cassette consisting of a promoter functional in the host cell operably linked to a DNA sequence encoding a polypeptide having three zinc finger domains, wherein the DNA sequence encodes the polypeptide of SEQ ID NO:2.

16. The host cell of claim 15 wherein the DNA sequence comprises SEQ ID NO:1.

17. The host cell of claim 16 wherein the DNA sequence consists of SEQ ID NO:1.

18. The host cell of claim 15 wherein the cell is a prokaryotic cell.

19. The host cell of claim 15 wherein the cell is a eukaryotic cell.

* * * * *

UNITED STATES PATENT AND TRADEMARK OFFICE
CERTIFICATE OF CORRECTION

PATENT NO.: 5,981,217

DATED: Nov. 9, 1999

INVENTOR(S): Subramaniam et al.

It is certified that error appears in the above-identified patent and that said Letters Patent is hereby corrected as shown below:

In column 23, line 39 insert paragraph break after "is:"

In column 23, line 51 insert paragraph break after "polypeptide."

In column 23, line 53 insert paragraph break after "sequence."

In column 23, line 55 insert paragraph break after "No: 1."

In column 23, line 56 insert paragraph break after "No: 1."

In column 23, line 60 insert paragraph break after "No: 2."

In column 23, line 64 insert paragraph break after "No: 1."

In column 23, line 66 insert paragraph break after "No: 1."

In column 24, line 42 insert paragraph break after "No: 1."

In column 24, line 45 insert paragraph break after "Claim 9."

In column 24, line 53 insert paragraph break after "Claim 9."

In column 24, line 59 insert paragraph break after "No: 2."

In column 24, line 61 insert paragraph break after "No: 1."

In column 24, line 63 insert paragraph break after "No: 1."

UNITED STATES PATENT AND TRADEMARK OFFICE
CERTIFICATE OF CORRECTION

PATENT NO. : 5,981,217
DATED : November 9, 1999
INVENTOR(S) : Subramaniam et al.

It is certified that error appears in the above-identified patent and that said Letters Patent is hereby corrected as shown below:

In column 25, line 2 insert paragraph break after "No: 2."

In column 25, line 4 insert paragraph break after "No: 1."

In column 25, line 5 insert paragraph break after "No: 1."

In column 26, line 2 insert paragraph break after "cell."

Signed and Sealed this

Sixth Day of March, 2001

Attest:

Attesting Officer

NICHOLAS P. GODICI

Acting Director of the United States Patent and Trademark Office